United States Patent
Nishina et al.

(10) Patent No.: US 8,493,057 B2
(45) Date of Patent: Jul. 23, 2013

(54) ELECTROMAGNETIC WAVE MEASURING APPARATUS, MEASURING METHOD, PROGRAM, AND RECORDING MEDIUM

(75) Inventors: Shigeki Nishina, Miyagi (JP); Motoki Imamura, Miyagi (JP); Akiyoshi Irisawa, Miyagi (JP); Tomoyu Yamashita, Miyagi (JP); Eiji Kato, Miyagi (JP); Kodo Kawase, Aichi (JP)

(73) Assignee: Advantest Corporation, Tokyo (JP)

( * ) Notice: Subject to any disclaimer, the term of this patent is extended or adjusted under 35 U.S.C. 154(b) by 716 days.

(21) Appl. No.: 12/731,483

(22) Filed: Mar. 25, 2010

(65) Prior Publication Data

US 2010/0295534 A1 Nov. 25, 2010

(30) Foreign Application Priority Data

May 15, 2009 (JP) ................................. 2009-118861

(51) Int. Cl.
*G01S 3/02* (2006.01)
(52) U.S. Cl.
USPC ............. 324/76.14; 324/76.56; 324/250; 324/754.22; 324/754.29; 250/208.1; 250/310; 250/311; 250/358.1; 250/360.1

(58) Field of Classification Search
USPC ............. 324/754.22, 754.29, 637–639, 715, 324/722.724; 250/208.1, 310, 311, 358.1, 250/360.1, 370.04, 370.09, 393, 395, 491.1, 250/336.1, 370.06

See application file for complete search history.

(56) References Cited

U.S. PATENT DOCUMENTS

| | | | |
|---|---|---|---|
| 7,119,339 B2 | 10/2006 | Ferguson et al. | |
| 8,183,528 B2 * | 5/2012 | Kato et al. | 250/358.1 |
| 2006/0219922 A1 | 10/2006 | Watanabe et al. | |
| 2008/0116374 A1 | 5/2008 | Ouchi et al. | |
| 2009/0153457 A1 * | 6/2009 | Kato | 345/89 |
| 2011/0241699 A1 * | 10/2011 | Itsuji | 324/629 |

FOREIGN PATENT DOCUMENTS

| | | |
|---|---|---|
| JP | 2004-286716 | 10/2004 |
| JP | 2008-116439 | 5/2008 |
| JP | 2009-056140 | 3/2009 |

OTHER PUBLICATIONS

S. Wang et al., "Pulsed terahertz tomography," J. Phys. D: Appl. Phys., vol. 37, pp. R1-R36, Jan. 28, 2004.
U.S. Appl. No. 12/487,177 to Kato et al., filed Jun. 18, 2009.
U.S. Appl. No. 12/731,617 to Nishina et al., filed Mar. 25, 2010.
Wang S et al., "Pulsed terahertz tomography", Journal of Physics D-Applied Physics, Feb. 21, 2004, vol. 37, R1-R36.

* cited by examiner

*Primary Examiner* — Arleen M Vasquez
*Assistant Examiner* — Son Le
(74) *Attorney, Agent, or Firm* — Greenblum & Bernstein, P.L.C.

(57) ABSTRACT

A detector detects an electromagnetic wave having a frequency of $0.01\,\text{THz} \leq f \leq 100\,\text{THz}$ and transmitted through a device under test (DUT). A changer changes a relative position of an intersection of an optical path of the electromagnetic wave and the DUT, with respect to the DUT. A deriver derives a characteristic value of the electromagnetic wave based on a detection result of the detector, while the characteristic value is associated with an assumed relative position, which is the relative position if the electromagnetic wave is not refracted by the DUT. A corrector changes the assumed relative position to an actual relative position, which is the relative position if the refraction of the electromagnetic wave by the DUT is considered. A corrected deriver derives the characteristic value associated with a predetermined relative position based on an output from the corrector.

10 Claims, 15 Drawing Sheets

ELECTROMAGNETIC WAVE MEASURING APPARATUS, MEASURING METHOD, PROGRAM, AND RECORDING MEDIUM

BACKGROUND ART

1. Field of the Invention

The present invention relates to tomography using an electromagnetic wave (frequency thereof is equal to or more than 0.01 [THz], and equal to or less than 100 [THz]) (such as a terahertz wave (frequency thereof is equal to or more than 0.03 [THz], and equal to or less than 10 [THz]), for example).

2. Description of the Prior Art

There has conventionally been the computed tomography (CT) as a method for obtaining tomographic information on a device under test. This method conducted while a generator and a detector of the X ray are used is referred to as X-ray CT. With the X-ray CT, it is possible to acquire tomographic information on a human body in non-destructive and non-contact manner.

However, it is difficult for the X-ray CT to detect internal states (such as defects and distortions) of industrial products constructed by semiconductors, plastics, ceramics, woods, and papers (referred to as "raw materials" hereinafter). This is because the X-ray presents a high transmission property to any materials.

On the other hand, the terahertz wave properly transmits through the raw materials of the industrial products described above. Therefore, the CT carried out while a generator and a detector of the terahertz wave are used (referred to as "terahertz CT" hereinafter) can detect internal states of the industrial products. Patent Document 1 and Non-Patent Document 1 describe the terahertz CT.

(Patent Document 1) U.S. Pat. No. 7,119,339
(Non-Patent Document 1) S. Wang et al., "Pulsed terahertz tomography," J. Phys. D, Vol. 37 (2004), R1-R36

SUMMARY OF THE INVENTION

However, according to the terahertz CT, when the terahertz wave is obliquely made incident to or emitted from a device under test (DUT), the terahertz wave is refracted, and thus does not travel straight. On this occasion, it is assumed that the refractive index of the ambient air of the DUT is 1, and the refractive index of the DUT for the terahertz CT is more than 1.

Due to the fact that the terahertz wave does not travel straight, the terahertz wave cannot reach a detector, and an image of the DUT cannot thus be obtained at a sufficient sensitivity.

Moreover, due to the fact that the terahertz wave does not travel straight, a detected terahertz wave may not have traveled straight through the DUT before the arrival. Therefore, when an image of the DUT is obtained from the detected terahertz wave, artifacts such as obstructive shadows and pseudo images may appear on the image.

Therefore, it is an object of the present invention, when an electromagnetic wave (frequency thereof is equal to or more than 0.01 [THz] and equal to or less than 100 [THz]) including the terahertz wave is fed to a DUT for measurement, to restrain an adverse effect caused by refraction of the electromagnetic wave including the terahertz wave by the DUT.

According to the present invention, an electromagnetic wave measurement device includes: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; a relative position changing unit that changes a relative position of an intersection across which an optical path of the electromagnetic wave transmitting through the device under test and the device under test intersect with respect to the device under test; a characteristic value deriving unit that derives a characteristic value of the electromagnetic wave based on a detection result of the electromagnetic wave detector while the characteristic value is associated with an assumed relative position which is the relative position if it is assumed that the electromagnetic wave is not refracted by the device under test; a first association correction unit that changes the assumed relative position to an actual relative position, which is the relative position if the refraction of the electromagnetic wave by the device under test is considered, thereby associating the result derived by the characteristic value deriving unit with the actual relative position; and a corrected characteristic value deriving unit that derives the characteristic value associated with a predetermined relative position based on an output from the first association correction unit.

According to the thus constructed electromagnetic wave measurement device, an electromagnetic wave output device outputs an electromagnetic wave having a frequency equal to or more than 0.01 [THz] and equal to or less than 100 [THz] toward a device under test. An electromagnetic wave detector detects the electromagnetic wave which has transmitted through the device under test. A relative position changing unit changes a relative position of an intersection across which an optical path of the electromagnetic wave transmitting through the device under test and the device under test intersect with respect to the device under test. A characteristic value deriving unit derives a characteristic value of the electromagnetic wave based on a detection result of the electromagnetic wave detector while the characteristic value is associated with an assumed relative position which is the relative position if it is assumed that the electromagnetic wave is not refracted by the device under test. A first association correction unit changes the assumed relative position to an actual relative position, which is the relative position if the refraction of the electromagnetic wave by the device under test is considered, thereby associating the result derived by the characteristic value deriving unit with the actual relative position. A corrected characteristic value deriving unit that derives the characteristic value associated with a predetermined relative position based on an output from the first association correction unit.

According to the present invention, an electromagnetic wave measurement device includes: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; a relative position changing unit that changes a relative position of an intersection across which an optical path of the electromagnetic wave transmitting through the device under test and the device under test intersect with respect to the device under test so that the intersection is at a predetermined relative position considering the refraction of the electromagnetic wave by the device under test; and a characteristic value deriving unit that derives a characteristic value of the electromagnetic wave based on a detection result of the electromagnetic wave detector while the characteristic value is associated with the predetermined relative position.

According to the thus constructed electromagnetic wave measurement device, an electromagnetic wave output device outputs an electromagnetic wave having a frequency equal to or more than 0.01 [THz] and equal to or less than 100 [THz] toward a device under test. An electromagnetic wave detector detects the electromagnetic wave which has transmitted through the device under test. A relative position changing unit changes a relative position of an intersection across which an optical path of the electromagnetic wave transmitting through the device under test and the device under test intersect with respect to the device under test so that the intersection is at a predetermined relative position considering the refraction of the electromagnetic wave by the device under test. A characteristic value deriving unit derives a characteristic value of the electromagnetic wave based on a detection result of the electromagnetic wave detector while the characteristic value is associated with the predetermined relative position.

According to the present invention, an electromagnetic wave measurement device includes: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; a relative position changing unit that changes a relative position of an intersection across which an optical path of the electromagnetic wave transmitting through the device under test and the device under test intersect with respect to the device under test; a characteristic value deriving unit that derives a characteristic value of the electromagnetic wave based on a detection result of the electromagnetic wave detector while the characteristic value is associated with an assumed relative position which is the relative position if it is assumed that the electromagnetic wave is not refracted by the device under test; and a second association correction unit that, while the relative position if a refraction of the electromagnetic wave by the device under test is considered is an actual relative position, acquires the characteristic value associated with the assumed relative position corresponding to the actual relative position closest to a predetermined relative position from the characteristic value deriving unit, and associates the acquired characteristic value with the predetermined relative position.

According to the thus constructed electromagnetic wave measurement device, an electromagnetic wave output device outputs an electromagnetic wave having a frequency equal to or more than 0.01 [THz] and equal to or less than 100 [THz] toward a device under test. An electromagnetic wave detector detects the electromagnetic wave which has transmitted through the device under test. A relative position changing unit changes a relative position of an intersection across which an optical path of the electromagnetic wave transmitting through the device under test and the device under test intersect with respect to the device under test. A characteristic value deriving unit derives a characteristic value of the electromagnetic wave based on a detection result of the electromagnetic wave detector while the characteristic value is associated with an assumed relative position which is the relative position if it is assumed that the electromagnetic wave is not refracted by the device under test. A second association correction unit, while the relative position if a refraction of the electromagnetic wave by the device under test is considered is an actual relative position, acquires the characteristic value associated with the assumed relative position corresponding to the actual relative position closest to a predetermined relative position from the characteristic value deriving unit, and associates the acquired characteristic value with the predetermined relative position.

According to the electromagnetic wave measurement device of the present invention, the characteristic value may be any one of an attenuation ratio, a group delay, and a chromatic dispersion of the electromagnetic wave.

According to the electromagnetic wave measurement device of the present invention, the relative position may be represented by an angle between the intersection and a predetermined axis, and a coordinate of an orthogonal axis orthogonal to the predetermined axis at an intersection point between the orthogonal axis and the intersection.

The present invention is an electromagnetic wave measurement method using an electromagnetic wave measurement device including: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; and a relative position changing unit that changes a relative position of an intersection across which an optical path of the electromagnetic wave transmitting through the device under test and the device under test intersect with respect to the device under test; the method including: a characteristic value deriving step that derives a characteristic value of the electromagnetic wave based on a detection result of the electromagnetic wave detector while the characteristic value is associated with an assumed relative position which is the relative position if it is assumed that the electromagnetic wave is not refracted by the device under test; a first association correction step that changes the assumed relative position to an actual relative position, which is the relative position if the refraction of the electromagnetic wave by the device under test is considered, thereby associating the result derived by the characteristic value deriving step with the actual relative position; and a corrected characteristic value deriving step that derives the characteristic value associated with a predetermined relative position based on a result from the first association correction step.

The present invention is an electromagnetic wave measurement method using an electromagnetic wave measurement device including: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; and a relative position changing unit that changes a relative position of an intersection across which an optical path of the electromagnetic wave transmitting through the device under test and the device under test intersect with respect to the device under test so that the intersection is at a predetermined relative position considering the refraction of the electromagnetic wave by the device under test; the method including: a characteristic value deriving step that derives a characteristic value of the electromagnetic wave based on a detection result of the electromagnetic wave detector while the characteristic value is associated with the predetermined relative position.

The present invention is an electromagnetic wave measurement method using an electromagnetic wave measurement device including: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; and a relative position changing unit that changes a relative position of an intersection across which an optical path of the electromagnetic wave transmitting through the device under test and the device under test intersect with respect to the device under test; the method including: a characteristic value deriving step that derives a characteristic value of the electromagnetic wave based on a detection result of the electromagnetic wave detector while the characteristic value is associated with an assumed relative position which is the relative position if it is assumed that the electromagnetic wave is not refracted by the device under test; and a second association correction step that, while the relative position if a refraction of the electromagnetic wave by the device under test is considered is an actual relative position, acquires the characteristic value associated with the assumed relative position corresponding to the actual relative position closest to a predetermined relative position from the result derived by the characteristic value deriving step, and associates the acquired characteristic value with the predetermined relative position.

The present invention is a program of instructions for execution by a computer to perform an electromagnetic wave measurement process using an electromagnetic wave measurement device including: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; and a relative position changing unit that changes a relative position of an intersection across which an optical path of the electromagnetic wave transmitting through the device under test and the device under test intersect with respect to the device under test; the electromagnetic wave measurement process including: a characteristic value deriving step that derives a characteristic value of the electromagnetic wave based on a detection result of the electromagnetic wave detector while the characteristic value is associated with an assumed relative position which is the relative position if it is assumed that the electromagnetic wave is not refracted by the device under test; a first association correction step that changes the assumed relative position to an actual relative position, which is the relative position if the refraction of the electromagnetic wave by the device under test is considered, thereby associating the result derived by the characteristic value deriving step with the actual relative position; and a corrected characteristic value deriving step that derives the characteristic value associated with a predetermined relative position based on a result from the first association correction step.

The present invention is a program of instructions for execution by a computer to perform an electromagnetic wave measurement process using an electromagnetic wave measurement device including: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; and a relative position changing unit that changes a relative position of an intersection across which an optical path of the electromagnetic wave transmitting through the device under test and the device under test intersect with respect to the device under test so that the intersection is at a predetermined relative position considering the refraction of the electromagnetic wave by the device under test; the electromagnetic wave measurement process including: a characteristic value deriving step that derives a characteristic value of the electromagnetic wave based on a detection result of the electromagnetic wave detector while the characteristic value is associated with the predetermined relative position.

The present invention is a program of instructions for execution by a computer to perform an electromagnetic wave measurement process using an electromagnetic wave measurement device including: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; and a relative position changing unit that changes a relative position of an intersection across which an optical path of the electromagnetic wave transmitting through the device under test and the device under test intersect with respect to the device under test; the electromagnetic wave measurement process including: a characteristic value deriving step that derives a characteristic value of the electromagnetic wave based on a detection result of the electromagnetic wave detector while the characteristic value is associated with an assumed relative position which is the relative position if it is assumed that the electromagnetic wave is not refracted by the device under test; and a second association correction step that, while the relative position if a refraction of the electromagnetic wave by the device under test is considered is an actual relative position, acquires the characteristic value associated with the assumed relative position corresponding to the actual relative position closest to a predetermined relative position from the result derived by the characteristic value deriving step, and associates the acquired characteristic value with the predetermined relative position.

The present invention is a computer-readable medium having a program of instructions for execution by a computer to perform an electromagnetic wave measurement process using an electromagnetic wave measurement device including: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; and a relative position changing unit that changes a relative position of an intersection across which an optical path of the electromagnetic wave transmitting through the device under test and the device under test intersect with respect to the device under test; the electromagnetic wave measurement process including: a characteristic value deriving step that derives a characteristic value of the electromagnetic wave based on a detection result of the electromagnetic wave detector while the characteristic value is associated with an assumed relative position which is the relative position if it is assumed that the electromagnetic wave is not refracted by the device under test; a first association correction step that changes the assumed relative position to an actual relative position, which is the relative position if the refraction of the electromagnetic wave by the device under test is considered, thereby associating the result derived by the characteristic value deriving step with the actual relative position; and a corrected characteristic value deriving step that derives the characteristic value associated with a predetermined relative position based on a result from the first association correction step.

The present invention is a computer-readable medium having a program of instructions for execution by a computer to perform an electromagnetic wave measurement process using an electromagnetic wave measurement device including: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; and a relative position changing unit that changes a relative position of an intersection across which an optical path of the electromagnetic wave transmitting through the device under test and the device under test intersect with respect to the device under test so that the intersection is at a predetermined relative position considering the refraction of the electromagnetic wave by the device under test; the electromagnetic wave measurement process including: a characteristic value deriving step that derives a characteristic value of the electromagnetic wave based on a detection result of the electromagnetic wave detector while the characteristic value is associated with the predetermined relative position.

The present invention is a computer-readable medium having a program of instructions for execution by a computer to perform an electromagnetic wave measurement process using an electromagnetic wave measurement device including: an electromagnetic wave output device that outputs an electromagnetic wave having a frequency equal to or more than 0.01 [THz] and equal to or less than 100 [THz] toward a device under test; an electromagnetic wave detector that detects the electromagnetic wave which has transmitted through the device under test; and a relative position changing unit that changes a relative position of an intersection across which an optical path of the electromagnetic wave transmitting through the device under test and the device under test intersect with respect to the device under test; the electromagnetic wave measurement process including: a characteristic value deriving step that derives a characteristic value of the electromagnetic wave based on a detection result of the electromagnetic wave detector while the characteristic value is associated with an assumed relative position which is the relative position if it is assumed that the electromagnetic wave is not refracted by the device under test; and a second association correction step that, while the relative position if a refraction of the electromagnetic wave by the device under test is considered is an actual relative position, acquires the characteristic value associated with the assumed relative position corresponding to the actual relative position closest to a predetermined relative position from the result derived by the characteristic value deriving step, and associates the acquired characteristic value with the predetermined relative position.

BEST MODE FOR CARRYING OUT THE INVENTION

A description will now be given of embodiments of the present invention with reference to drawings.

First Embodiment

Figure 1:
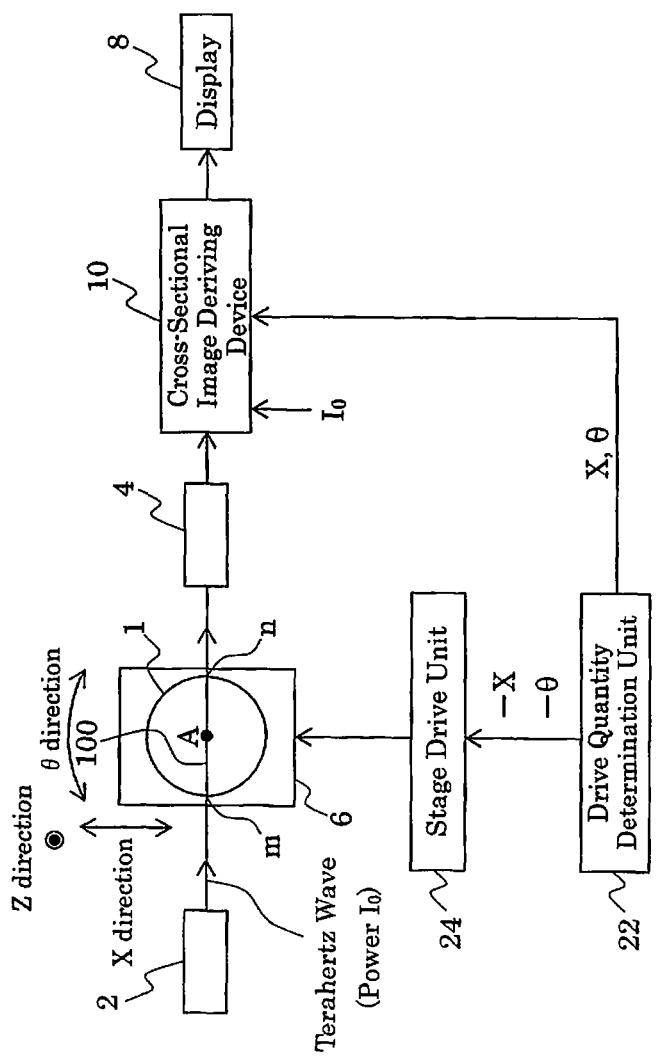
FIG. 1 is a diagram showing a configuration of an electromagnetic wave measurement device according to a first embodiment of the present invention.

FIG. 1 is a diagram showing a configuration of an electromagnetic wave measurement device according to a first embodiment of the present invention. The electromagnetic wave measurement device according to the first embodiment includes an electromagnetic wave output device 2, an electromagnetic wave detector 4, a stage for scanning (relative position changing unit) 6, a display 8, a cross-sectional image deriving device 10, a drive quantity determination unit 22, and a stage drive unit 24. The electromagnetic wave measurement device is used for measuring a device under test (DUT) 1.

The electromagnetic wave output device 2 outputs an electromagnetic wave having a frequency equal to or more than 0.01 [THz] and equal to or less than 100 [THz] toward the DUT 1. The frequency of the electromagnetic wave output toward the DUT 1 includes a terahertz wave band (such as equal to or more than 0.03 [THz] and equal to or less than 10 [THz]). According to the embodiment of the present invention, it is assumed to employ a terahertz wave as an example of the electromagnetic wave. A power of the electromagnetic wave output toward the DUT 1 is $I_0$.

The terahertz wave output to the DUT 1 transmits through the DUT 1. The electromagnetic wave detector 4 detects the electromagnetic wave (such as a terahertz wave) which has transmitted through the DUT 1.

A point at which the terahertz wave is made incident to the DUT 1 is m, and a point at which the terahertz wave is emitted from the DUT 1 is n. Then, an intersection 100 between an optical path of the electromagnetic wave which transmits through the DUT 1 and the DUT 1 is represented as a line mn. Moreover, a planar cross sectional shape of the DUT 1 is circular, and the center of the circle is a point A.

It should be noted that all points m1, m2, m3, and m4 are points at which the terahertz wave is made incident to the DUT 1. All points n1, n2, n3, and n4 are points at which the terahertz wave is emitted from the DUT 1.

The stage for scanning (relative position changing unit) 6 changes a relative position of the intersection 100 with respect to the DUT 1. For example, the DUT 1 is fixed to the stage for scanning 6, the stage for scanning 6 moves in the X direction and the Z direction (direction perpendicular to the sheet of FIG. 1), and rotates about a line which passes through the point A, and is perpendicular to the sheet of FIG. 1 (referred to as "movement in the θ direction").

Figure 2:
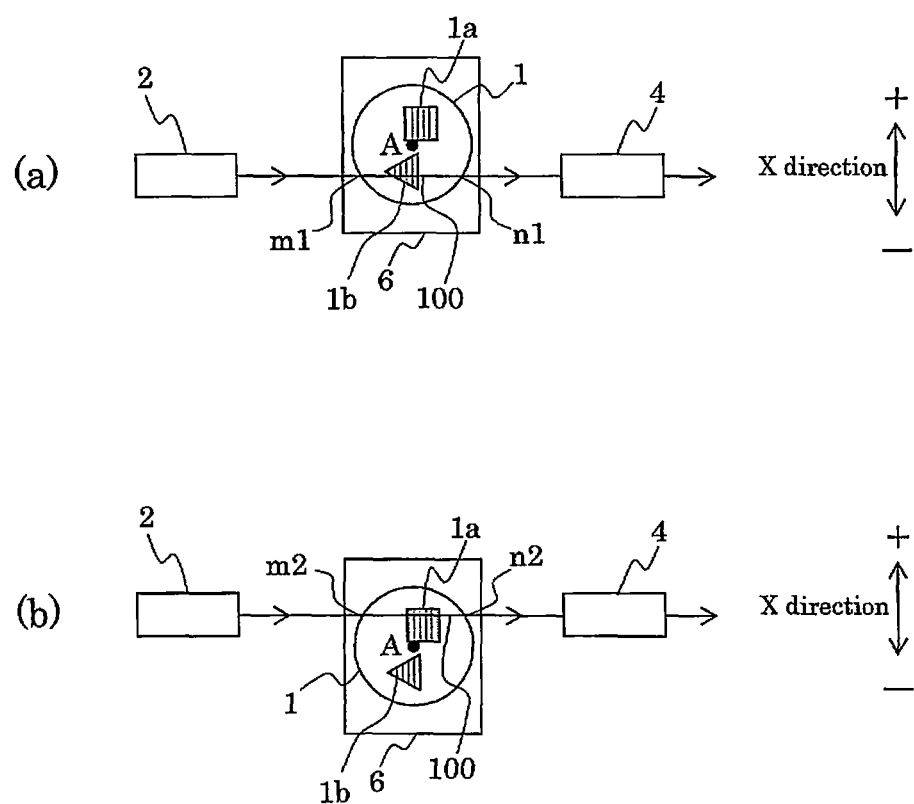
FIGS. 2(a) and 2(b) are a plan view of the DUT 1, the electromagnetic wave output device 2, the electromagnetic wave detector 4, and the stage for scanning 6, when the stage for scanning 6 is moved in the X direction.

FIGS. 2(a) and 2(b) are a plan view of the DUT 1, the electromagnetic wave output device 2, the electromagnetic wave detector 4, and the stage for scanning 6, when the stage for scanning 6 is moved in the X direction. It should be noted that the DUT 1 contains contents 1a and 1b.

Referring to FIG. 2(a), when the stage for scanning 6 is moved in the +X direction from the state shown in FIG. 1 (alternatively, the electromagnetic wave output device 2 and the electromagnetic wave detector 4 may be moved in the −X direction), the intersection 100 is represented by a line m1n1. The relative position of the intersection 100 with respect to the DUT 1 is below the point A. The intersection 100 passes through the content 1b.

Referring to FIG. 2(b), when the stage for scanning 6 is moved in the −X direction from the state shown in FIG. 1 (alternatively, the electromagnetic wave output device 2 and the electromagnetic wave detector 4 may be moved in the +X direction), the intersection 100 is represented by a line m2n2. The relative position of the intersection 100 with respect to the DUT 1 is above the point A. The intersection 100 passes through the content 1a.

When the stage for scanning 6 is moved in the X direction, thereby changing the state from that shown in FIG. 2(a) to that shown in FIG. 2(b), the relative position of the intersection 100 with respect to the DUT 1 changes from that below the point A to that above the point A.

Figure 3:
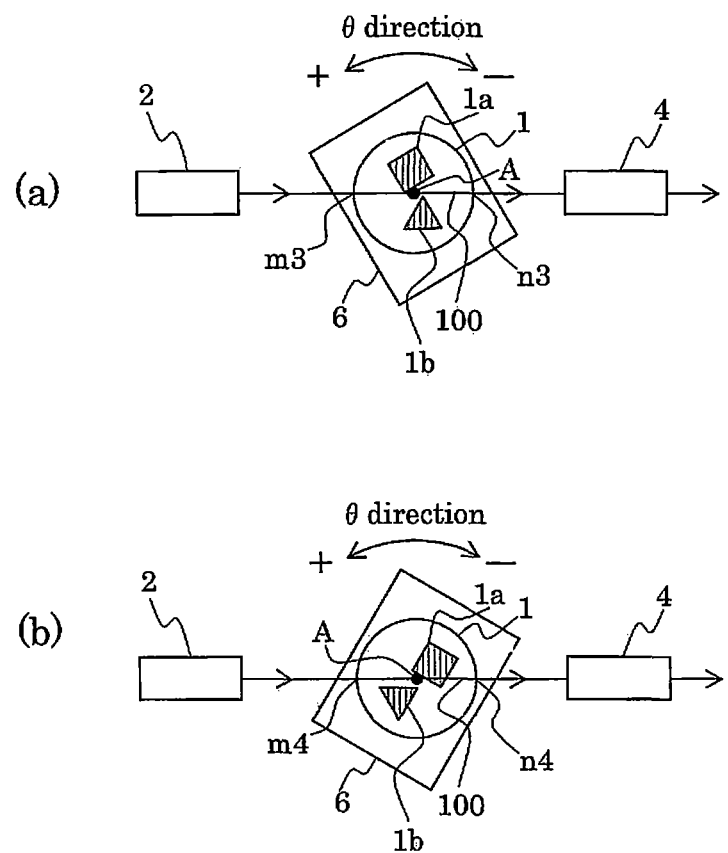
FIGS. 3(a) and 3(b) are plan views of the DUT 1, the electromagnetic wave output device 2, the electromagnetic wave detector 4, and the stage for scanning 6, when the stage for scanning 6 is moved in the θ direction.

FIGS. 3(a) and 3(b) are plan views of the DUT 1, the electromagnetic wave output device 2, the electromagnetic wave detector 4, and the stage for scanning 6, when the stage for scanning 6 is moved in the θ direction. It should be noted that the DUT 1 contains the contents 1a and 1b.

Referring to FIG. 3(a), when the stage for scanning 6 is moved in the +θ direction from the state shown in FIG. 1 (alternatively, the electromagnetic wave output device 2 and the electromagnetic wave detector 4 may be moved in the −θ direction), the intersection 100 is represented by a line m3n3. The intersection 100 passes between the content 1a and the content 1b.

Referring to FIG. 3(b), when the stage for scanning 6 is moved in the −θ direction from the state shown in FIG. 1 (alternatively, the electromagnetic wave output device 2 and the electromagnetic wave detector 4 may be moved in the +θ direction), the intersection 100 is represented by a line m4n4. The intersection 100 passes through the content 1a.

When the stage for scanning 6 is moved in the θ direction, thereby changing the state from that shown in FIG. 3(a) to that shown in FIG. 3(b), the relative position of the intersection 100 with respect to the DUT 1 changes.

As described above, the DUT 1 can be scanned by the stage for scanning 6.

The drive quantity determination unit 22 determines how much the stage for scanning 6 is driven in the X direction and the θ direction. On this occasion, it is assumed that a quantity of motion in the X direction of the stage for scanning 6 is −X, and a quantity of motion in the θ direction is −θ. Then, the drive quantity determination unit 22 feeds −X and −θ to the stage drive unit 24. The drive quantity determination unit 22 also feeds X and θ to the cross sectional image deriving device 10.

The stage drive unit 24 drives the stage for scanning 6 in the X direction and the θ direction by the quantities of motion (−X and −θ) fed by the drive quantity determination unit 22. As a result, the optical path of the electromagnetic wave traveling from the electromagnetic wave output device 2 to the DUT 1 is moved from X=0 by X in the X direction and from θ=0 by θ in the θ direction with respect to the DUT 1.

The drive quantity determination unit 22 feeds the quantities of motion (X and θ) of the optical path of the electromagnetic wave traveling from the electromagnetic wave output device 2 to the DUT 1 to the cross sectional image deriving device 10.

The cross sectional image deriving device 10 derives a cross sectional image of a cross section of the DUT 1 made on a plane containing the intersection 100 (the sheet in FIGS. 1, 2(a), 2(b), 3(a), and 3(b)).

The display 8 shows the cross sectional image derived by the cross sectional image deriving device 10. The derived cross sectional image is numerical data on the two-dimensional cross section of the DUT 1, and a two-dimensional tomographic cross sectional image of the DUT 1 is shown by associating the numerical data with predetermined colors. It should be noted that a widely known method may be properly employed as the method for displaying the two-dimensional tomographic cross sectional image based on numerical data.

Figure 4:
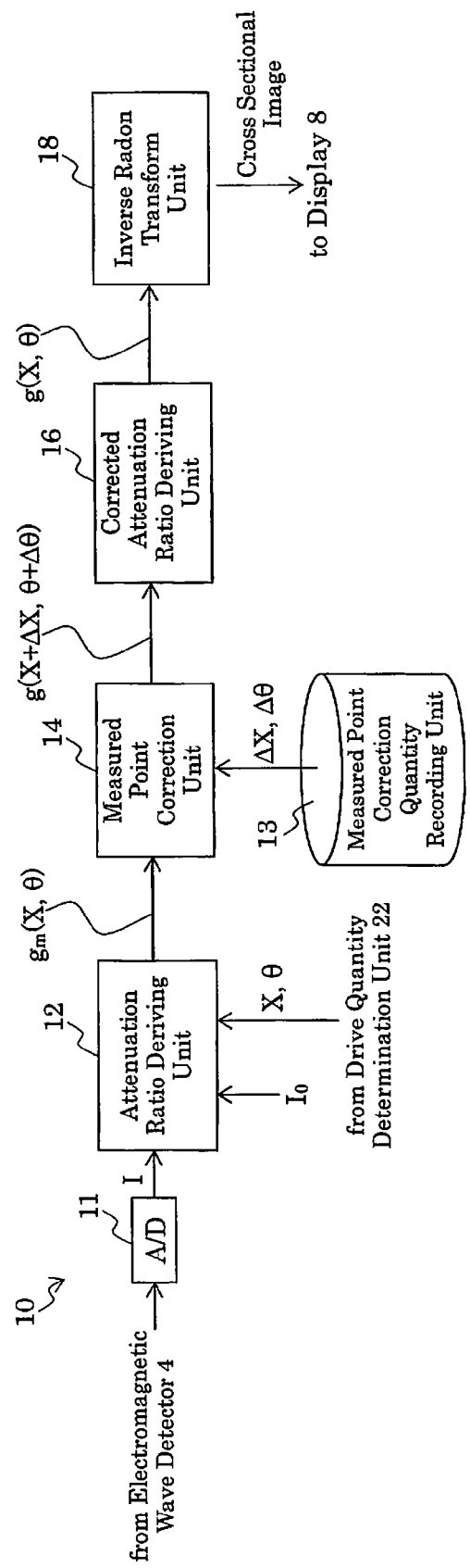
FIG. 4 is a functional block diagram showing a configuration of the cross sectional image deriving device 10 according to the first embodiment.

FIG. 4 is a functional block diagram showing a configuration of the cross sectional image deriving device 10 according to the first embodiment. The cross sectional image deriving device 10 includes an A/D converter 11, an attenuation ratio deriving unit (characteristic value deriving unit) 12, a measured point correction quantity recording unit 13, a measured point correction unit (first association correction unit) 14, a corrected attenuation ratio deriving unit (corrected characteristic value deriving unit) 16, and an inverse radon transform unit 18.

The A/D converter 11 converts a detected result of the electromagnetic wave detector 4, which is an analog signal, into a digital signal.

The attenuation ratio deriving unit (characteristic value deriving unit) 12 derives a characteristic value of the electromagnetic wave based on a detected result of the electromagnetic wave detector 4. The characteristic value is possibly any one of an attenuation ratio, a group delay, and a chromatic dispersion of the electromagnetic wave. After acquiring the phase of the electromagnetic wave from the detected result of the electromagnetic wave detector 4, the group delay of the electromagnetic wave can be derived by partially differentiating the phase by the frequency. The chromatic dispersion of the electromagnetic wave can be derived by partially differentiating the group delay of the electromagnetic wave by the frequency.

It should be noted that, in embodiments of the present invention, the attenuation ratio deriving unit (characteristic value deriving unit) 12 derives the attenuation ratio $g_m(X, \theta)$ of the electromagnetic wave.

Figure 5:
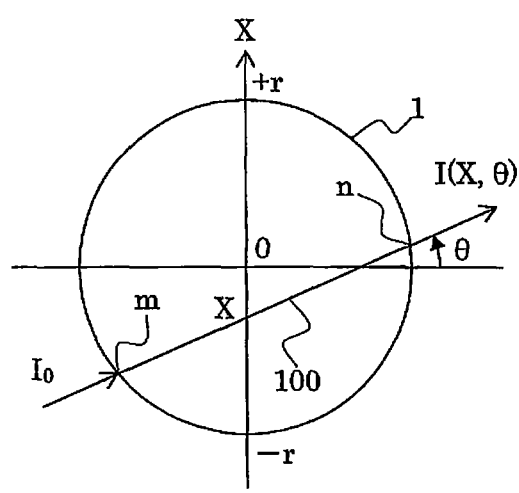
FIG. 5 is a plane cross sectional view showing an optical path of the electromagnetic wave passing though the DUT 1 assuming that the refraction does not occur for the sake of a description of the attenuation ratio of the electromagnetic wave.

FIG. 5 is a plane cross sectional view showing an optical path of the electromagnetic wave passing though the DUT 1 assuming that the refraction does not occur for the sake of a description of the attenuation ratio of the electromagnetic wave.

A power (intensity) of the electromagnetic wave traveling toward the DUT 1 is denoted by $I_0$ and a power of the electromagnetic wave after passing through the DUT 1 is denoted by $I(X, \theta)$. It should be noted that X denotes an X-axis intercept of an intersection 100. In other words, X denotes an X-axis coordinate of an intersection point between the X axis (orthogonal axis) and the intersection 100. Moreover, $\theta$ denotes an angle between the intersection 100 and a horizontal axis (predetermined axis) orthogonal to the X axis. The power of the electromagnetic wave which has transmitted through the DUT 1 is associated with $(X, \theta)$. The attenuation ratio of the electromagnetic wave is represented as $1n(I_0/I(X, \theta))$. It should be noted that $(X, \theta)$ represents a relative position of the intersection 100 with respect to the DUT 1.

The attenuation ratio deriving unit 12 acquires the power $I(X, \theta)$ of the electromagnetic wave which has transmitted through the DUT 1 from the A/D converter 11. X and $\theta$ are acquired from the drive quantity determination unit 22.

On this occasion, it is assumed that a planar cross section of the DUT 1 is a circle having a radius r. Then, the value of X ranges from -r to +r, and the value of $\theta$ ranges from $-\pi$[rad] to $+\pi$[rad]. On this occasion, X and $\theta$ are changed within the above respective ranges, thereby deriving the attenuation ratio $g_m(X, \theta)$. As the power $I_0$ of the electromagnetic wave traveling toward the DUT 1, a known value is fed to the attenuation ratio deriving unit 12 when the DUT 1 is measured.

Figure 6:
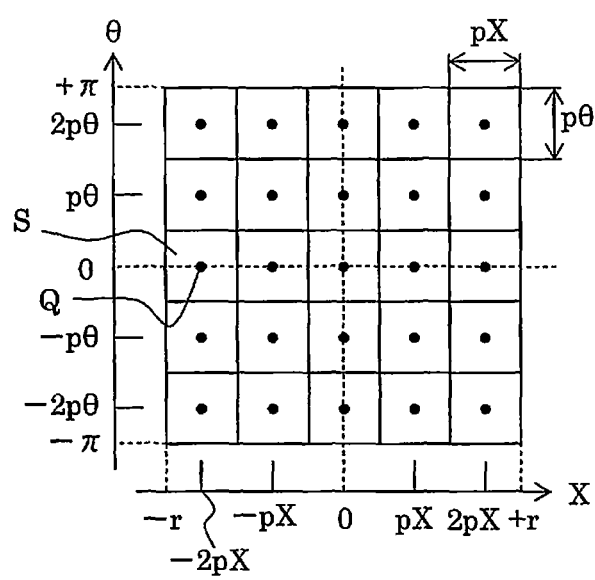
FIG. 6 shows a measured point (X, θ) for deriving the attenuation ratio $g_m(X, \theta)$.

FIG. 6 shows a measured point $(X, \theta)$ for deriving the attenuation ratio $g_m(X, \theta)$. FIG. 6 shows $(X, \theta)$, which is arguments of the attenuation ratio $g_m(X, \theta)$, on an X 0 coordinate plane in which $\theta$ is assigned to the vertical axis, and X is assigned to the horizontal axis. On this occasion, $(X, \theta)$ is referred to as measured point. The attenuation ratio $g_m(X, \theta)$ derived by the attenuation ratio deriving unit 12 is associated with the measured point $(X, \theta)$.

In FIG. 6, for the sake of simple illustration, X (X coordinate of the intersection point between the intersection 100 and the X axis) takes values -2pX, -pX, 0, pX, and 2pX, and $\theta$ (angle between the intersection 100 and the horizontal axis orthogonal to the X axis) takes values $-2p\theta$, $-p\theta$, 0, $p\theta$, and $2p\theta$. For these combinations of X and $\theta$ (5×5=25 combinations), the attenuation ratio deriving unit 12 derives the attenuation ratio $g_m(X, \theta)$. It should be noted that, in order to increase the accuracy of the attenuation ratio $g_m(X, \theta)$, the number of X and $\theta$ may be increased.

An attenuation ratio $g_m(X, \theta)$ corresponding to a black point in FIG. 6 represents an attenuation ratio in a rectangular area ($p\theta$ in height and pX in width) in FIG. 6. In other words, it is considered that the attenuation ratio corresponding to the rectangular area ($p\theta$ in height and pX in width) takes the value of the attenuation ratio $g_m(X, \theta)$ corresponding to the black point at the graphical center of the rectangle. For example, it is assumed that an attenuation ratio corresponding to the inside of a rectangle S ($p\theta$ in height and pX in width) having a black point Q at the graphic center takes a value of an attenuation ratio $g_m(-2pX, 0)$ corresponding to the black point Q.

It should be noted that, the measured point $(X, \theta)$, as described referring to FIG. 5, represents the relative position (referred to as "assumed relative position") when it is assumed that the DUT 1 does not refract the electromagnetic wave. Thus, the attenuation ratio deriving unit 12 derives the attenuation ratio $g_m(X, \theta)$ while the attenuation ratio $g_m(X, \theta)$ is associated with the assumed relative position (measured point $(X, \theta)$).

The measured point correction quantity recording unit 13 records a difference $\Delta X$ of the X coordinate and a difference $\Delta \theta$ of the $\theta$ coordinate between the measured point $(X, \theta)$ representing the assumed relative position and a measured point $(X', \theta')$ representing an actual relative position which is a relative position considering the refraction of the electromagnetic wave caused by the DUT 1.

Figure 7:
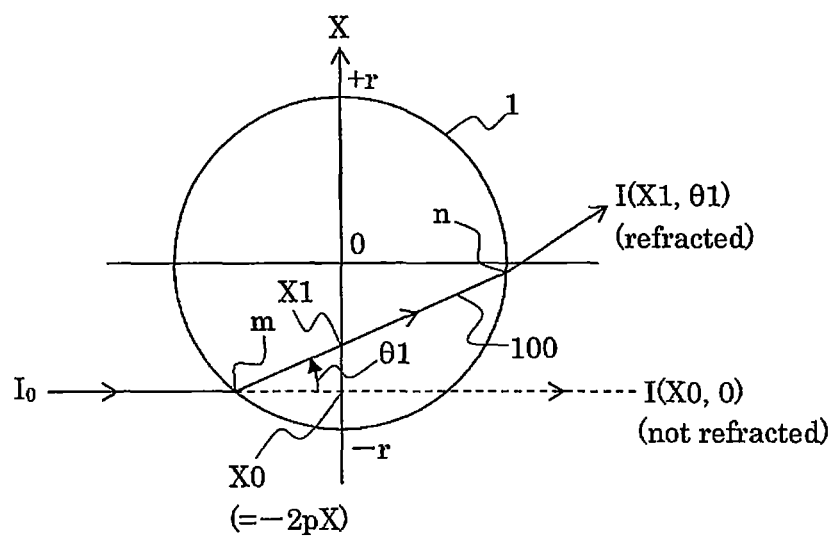
FIG. 7 is a plane cross sectional view representing the optical path of the electromagnetic wave passing through the DUT 1 for describing the assumed relative position and the actual relative position.

FIG. 7 is a plane cross sectional view representing the optical path of the electromagnetic wave passing through the DUT 1 for describing the assumed relative position and the actual relative position. It should be noted that a measured point representing the assumed relative position is denoted by Q(X0, 0) (X0=-2pX, refer to FIG. 6).

First, it is assumed that the electromagnetic wave is made incident to the DUT 1 orthogonally to the X axis, and the X-axis intercept in a traveling direction thereof is -2pX. Then, if the DUT 1 does not refract the electromagnetic wave, the assumed relative position (assuming the refraction is not present) of the intersection 100 is represented by a measured point (-2pX, 0).

However, the electromagnetic wave (such as terahertz wave) passing through the DUT 1 is refracted by the DUT 1. On this occasion, it is assumed that the refractive index of the ambient air of the DUT 1 is 1, and the refractive index of the DUT 1 is more than 1. Then, the traveling direction of the terahertz wave is changed at a point m by the refraction. First, an angle between the traveling direction of the terahertz wave and the horizontal axis changes from 0 [rad] to $\theta 1$ [rad]. It should be noted that $\theta 1 > 0$. Then, the X-axis intercept X1 of the intersection 100 is represented as X1>-2pX when the refraction is considered. In other words, the actual relative position of the intersection 100 is represented as the measured point (X1, $\theta 1$).

In this case, the measured point correction quantity recording unit 13 records $\Delta X = X1 - X0 = X1 + 2pX$ and $\Delta \theta = \theta 1 - 0 = \theta 1$ while $\Delta X$ and $\Delta \theta$ are associated with the assumed relative position (measured point (-2pX, 0)).

The X coordinate X1 of the measured point representing the actual relative position of the intersection 100 is acquired by adding $\Delta X$ to the X coordinate -2pX of the measured point representing the assumed relative position. The $\theta$ coordinate $\theta 1$ of the measured point representing the actual relative position of the intersection 100 is acquired by adding $\Delta \theta$ to the $\theta$ coordinate 0 of the measured point representing the assumed relative position.

The measured point correction unit (first association correction unit) 14 changes the assumed relative position to the actual relative position, thereby associating the result derived by the attenuation ratio deriving unit 12 with the actual relative position.

The measured point correction unit 14 receives the attenuation ratio $g_m(X, \theta)$ from the attenuation ratio deriving unit 12. On this occasion, the measured point $(X, \theta)$ represents the assumed relative position of the intersection 100. The measured point correction unit 14 reads $\Delta X$ and $\Delta \theta$ corresponding to the measured point $(X, \theta)$ from the measured point correction quantity recording unit 13. The measured point correction unit 14 adds $\Delta X$ to the X coordinate X of the measured point $(X, \theta)$, and adds $\Delta \theta$ to the $\theta$ coordinate $\theta$ of the measured point $(X, \theta)$, thereby acquiring the measured point $(X+\Delta X, \theta+\Delta \theta)$. This measured point $(X+\Delta X, \theta+\Delta \theta)$ represents the actual relative position of the intersection 100. For example, when X=−2pX and θ=0, the actual relative position is represented as the measured point (−2pX+ΔX, θ+Δθ)=(X1, θ1) as described above.

The measured point correction unit 14 changes the assumed relative position (represented by the measured point (X, θ)) of the attenuation ratio $g_m(X, θ)$ derived by the attenuation ratio deriving unit 12 to the actual relative position (represented by the measured point (X+ΔX, θ+Δθ)), thereby associating the attenuation ratio $g_m(X, θ)$ with the actual relative position (represented by the measured point (X+ΔX, θ+Δθ)). The attenuation ratio $g_m(X, θ)$ associated with the actual relative position is denoted by g(X+ΔX, θ+Δθ). In other words, an association g(X+ΔX, θ+Δθ)=$g_m(X, θ)$ is set. The measured point correction unit 14 outputs g(X+ΔX, θ+Δθ).

On this occasion, the measured point representing the assumed relative position is referred to as assumed measured point, and the measured point representing the actual relative position is referred to as actual measured point.

Figure 8:
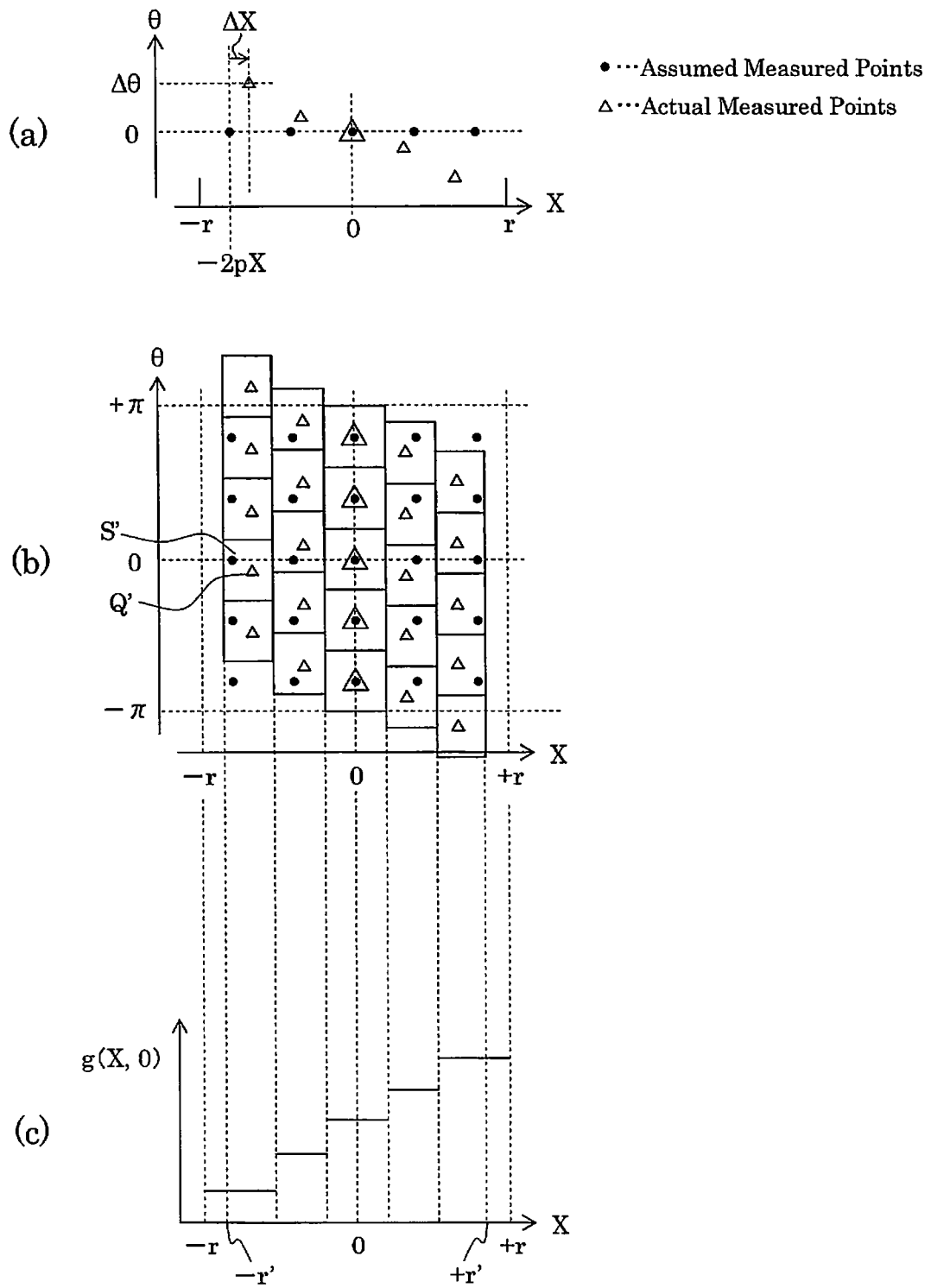
FIG. 8(a) shows assumed measured points and actual measured points when θ=θ.
FIG. 8(b) shows assumed measured points and corresponding actual measured points when θ=−2pθ, −pθ, 0, −pθ, and 2pθ.
FIG. 8(c) shows the attenuation ratio g(x, θ) when θ=0.

FIG. 8(*a*) shows assumed measured points and actual measured points when θ=0, FIG. 8(*b*) shows assumed measured points and corresponding actual measured points when θ=−2pθ, −pθ, 0, pθ, and 2pθ, and FIG. 8(*c*) shows the attenuation ratio g(x, 0) when θ=0.

Referring to FIG. 8(*a*), when the assumed measured point is (0, 0), an outer periphery of the DUT 1 is orthogonal to the optical path of the terahertz wave traveling toward the DUT 1, and, thus, the terahertz wave does not refract. Thus, when the assumed measured point is (0, 0), the actual measured point is (0, 0).

When the assumed measured point is (−2pX, 0), the X coordinate of the actual measured point is displaced by ΔX (=X1−X0=X1+2pX) in the X coordinate, and the θ coordinate of the actual measured point is displaced by Δθ(=θ1−0=θ1), and the actual measured point is (X1, θ1).

When the assumed measured point is (−pX, 0), the X coordinate of the actual measured point is slightly larger than −pX, and the θ coordinate is also slightly larger.

Actual measured points of the assumed measured points (2pX, 0) and (pX, 0) are point symmetric with the actual measured points of the assumed measured points (−2pX, 0) and (−pX, 0). It should be noted that the center of the point symmetry is (0, 0).

On this occasion, since the planar cross section of the DUT 1 is the circle, ΔX and Δθ are functions of the X coordinate of the assumed measured point. On the other hand, even when the θ coordinate of the assumed measured point changes, ΔX and Δθ are constant. Thus, as long as the X coordinate of the assumed measured point remains constant, ΔX and Δθ are constant.

It should be noted that the embodiment of the present invention can be applied to a case in which the planar cross section of the DUT 1 is not a circle. The embodiment of the present invention is applicable to a case in which ΔX and Δθ change when the θ coordinate of the assumed measured point changes.

In FIG. 8(*b*), an attenuation ratio associated with an actual measured point represents attenuation ratios in a rectangular area the graphic center of which is the actual measured point. In other words, the attenuation ratios corresponding to the rectangular area are represented by the attenuation ratio g(X+ΔX, θ+Δθ) corresponding to the actual measured point at the graphic center of the rectangle. For example, an attenuation ratio corresponding to the inside of a rectangle S' the graphic center of which is an actual measured point Q' is represented by an attenuation ratio corresponding to the actual measured point Q'.

It should be noted that the respective rectangles in FIG. 8(*b*) narrows as the rectangles approaches the ends in the direction of the X axis. This is because the optical path refracts more (the absolute value of Δθ increases) as the point approaches the ends on the X axis, and an interval in terms of the X-axis coordinate between neighboring actual measured points decreases. Therefore, the widths of areas represented by attenuation ratios for a certain θ are not even. This implies that widths of sampling are uneven.

For example, an attenuation ratio g(X, θ) when θ=0 is an attenuation ratio associated with an actual measured point located at the center of figure of a rectangle intersecting a line for θ=0 in FIG. 8(*b*) by the measured point correction unit 14. This attenuation ratio is shown in FIG. 8(*c*). It should be noted that the attenuation ratio can be known only in a range equal to or more than −r' and equal to or less than r' in the X-axis coordinate (0<r'<r). Then, though the attenuation ratio in a range equal to or more than −r and less than −r' may be set to 0 (zero), the attenuation ratio in this range is set to the same attenuation ratio that is in a range including −r'. Then, though the attenuation ratio in a range more than r' and equal to or less than r may be set to 0 (zero), the attenuation ratio in this range is set to the same attenuation ratio that is in a range including r'.

As is appreciated from the reference to FIG. 8(*c*), the sampling widths for θ=0 (corresponding to a horizontal solid lines in the chart) are not even.

The corrected attenuation ratio deriving unit (corrected characteristic value deriving unit) 16 derives a characteristic value (attenuation ratio g(X, θ)) associated with a predetermined relative position (such as an assumed measured point) based on the output from the measured point correction unit (first association correction unit) 14.

Figure 9:
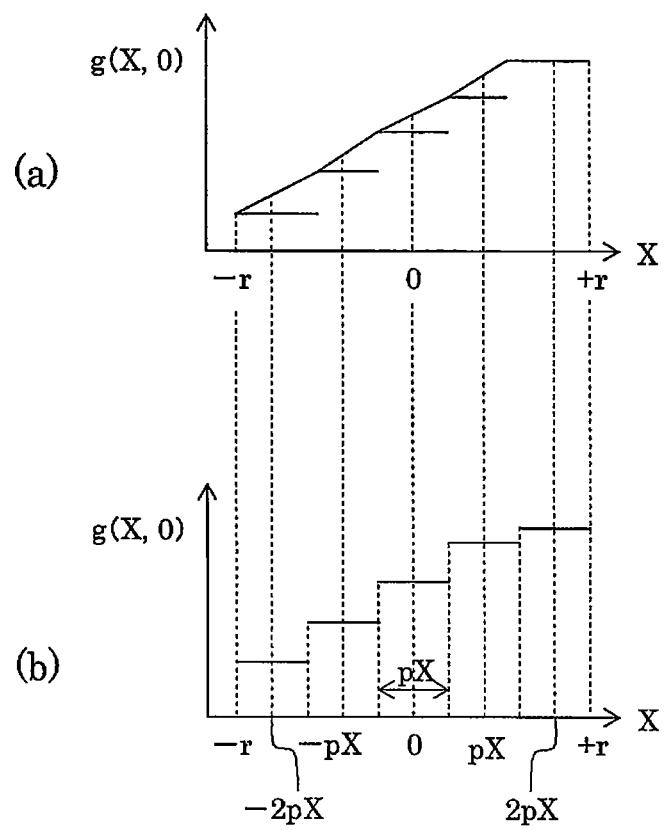
FIGS. 9(a) and 9(b) show a method for deriving the attenuation ratio g(X, θ) associated with the assumed measured point.

FIGS. 9(*a*) and 9(*b*) show a method for deriving the attenuation ratio g(X, θ) associated with the assumed measured point.

FIG. 9(*a*) is similar to FIG. 8(*c*). However, intermediate portions between left ends of the respective horizontal lines in the chart of FIG. 8(*c*) are linearly interpolated.

The corrected attenuation ratio deriving unit 16 acquires (samples) values at −2pX, −pX, 0, pX, and 2pX in the X coordinate from the attenuation ratio acquired by linearly interpolating the attenuation ratio having the uneven sampling widths as shown in FIG. 9(*a*). This results in even sampling widths pX as shown in FIG. 9(*b*).

It should be noted that the corrected attenuation ratio deriving unit 16 acquires values using the even sampling width pX for θ=−2pθ, −pθ, pθ, and 2pθ in addition to the case of θ=0.

However, it is appreciated that there is no area to which an actual measured point corresponds for θ=−2pθ at the left end (X coordinate is close to −r') (refer to FIG. 8(*b*)).

Figure 10:
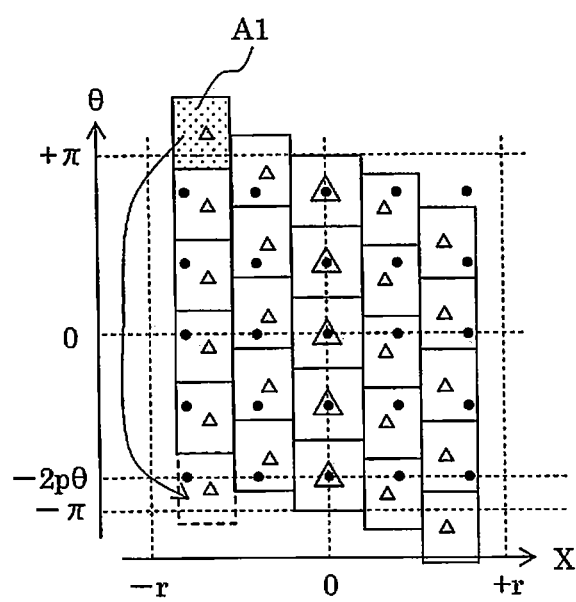
FIG. 10 describes an operation of the corrected attenuation ratio deriving unit 16 for θ=−2pθ.

FIG. 10 describes an operation of the corrected attenuation ratio deriving unit 16 for θ=−2pθ. The portion at the left end (the X coordinate of which is close to −r') takes an attenuation ratio associated with an actual measured point at the center of figure of a rectangle A1 separated by one cycle.

When the sampling widths in the θ direction for a certain X are uneven, by the method described referring to FIGS. 9(*a*) and 9(*b*), even sampling widths can be acquired in the θ direction.

The inverse radon transform unit 18 receives the attenuation ratio g(X, θ) associated with the assumed measured point (refer to FIG. 6) from the corrected attenuation ratio deriving unit 16, and performs the inverse radon transform, thereby acquiring a cross sectional image. The cross sectional image is fed to the display 8. It should be noted that the inverse radon transform unit 18 may determine predetermined colors to be associated with the cross sectional image, and may provide the determined colors to the display 8.

A description will now be given of an operation of the first embodiment.

First, the DUT 1 is fixed to the stage for scanning 6.

The drive quantity determination unit 22 determines how much the stage for scanning 6 is driven in the X direction and the B direction. The stage drive unit 24 drives the stage for scanning 6 in the X direction and the θ direction by the quantities of motion (−X and −θ) fed by the drive quantity determination unit 22. As a result, an optical path of the electromagnetic wave traveling from the electromagnetic wave output device 2 to the DUT 1 is moved from X=0 by X in the X direction and from θ=0 by θ in the θ direction with respect to the DUT 1. It should be noted that (X, θ) is the assumed measured point (refer to FIGS. 6 and 8).

On this occasion, while the stage for scanning 6 is moved in the X direction and the Z direction (direction perpendicular to the sheet of FIG. 1) as well as in the θ direction, the electromagnetic wave output device 2 outputs the electromagnetic wave having a frequency equal to or more than 0.01 [THz] and equal to or less than 100 [THz] (such as a terahertz wave) toward the DUT 1. The terahertz wave output to the DUT 1 transmits through the DUT 1. The electromagnetic wave which has passed through the DUT 1 is detected by the electromagnetic wave detector 4. In this way, the DUT 1 is scanned.

The detected result of the electromagnetic wave detector 4 is fed to the A/D converter 11 of the cross sectional image deriving device 10. The detected result of the electromagnetic wave detector 4 is converted by the A/D converter 11 into the digital signal, and the digital signal is fed to the attenuation ratio deriving unit 12.

The attenuation ratio deriving unit 12 derives the attenuation ratio $g_m(X, θ)$ associated with the assumed measured point (X, θ) where X=−2pX, −pX, 0, pX, and 2pX, and θ=−2pθ, −pθ, 0, pθ, and 2pθ (refer to FIGS. 6 and 8).

The measured point correction unit 14 reads ΔX and Δθ corresponding to the assumed measured point (X, θ) from the measured point correction quantity recording unit 13, and adds them respectively to X and θ, thereby converting the assumed measured point into an actual measured point. Then, the measured point correction unit 14 associates the attenuation ratio $g_m(X, θ)$ with the actual measured point (X+ΔX, θ+Δθ), thereby representing the attenuation ratio $g_m(X, θ)$ as g(X+ΔX, θ+Δθ). In other words, an association g(X+ΔX, θ+Δθ)=$g_m(X, θ)$ is set. For example, an association g(X1, θ1)=$g_m(−2pX, 0)$ is set. The measured point correction unit 14 outputs g(X+ΔX, θ+Δθ).

When g(X+ΔX, θ+Δθ) is considered for a certain θ (such as θ=0) (refer to FIG. 8(c)), the sampling widths in the X-axis direction are uneven. This is because the optical path refracts more (the absolute value of Δθ increases) as the point approaches the ends on the X axis, and an interval in terms of the X-axis coordinate between neighboring actual measured points decreases.

Thus, the corrected attenuation ratio deriving unit 16 samples g(X+ΔX, θ+Δθ) acquired from the measured point correction unit 14 at the even interval in terms of X axis (as well as θ axis according to necessity) (refer to FIGS. 9(a) and 9(b)). As a result, the corrected attenuation ratio deriving unit 16 derives the attenuation ratio g(X, θ) associated with the assumed measured point.

The attenuation ratio g(X, θ) output from the corrected attenuation ratio deriving unit 16 is transformed by the inverse radon transform unit 18 by means of the inverse radon transform, resulting in the cross sectional image. The cross sectional image is colored, and is then displayed by the display 8.

According to the first embodiment, when an electromagnetic wave (frequency thereof is equal to or more than 0.01 [THz] and equal to or less than 100 [THz]) including the terahertz wave is fed to the DUT 1 for measurement, it is possible to restrain the adverse effect caused by the refraction of the electromagnetic wave including the terahertz wave by the DUT 1 since the attenuation ratio is derived considering that the electromagnetic wave including the terahertz wave is refracted by the DUT 1.

Second Embodiment

Figure 11:
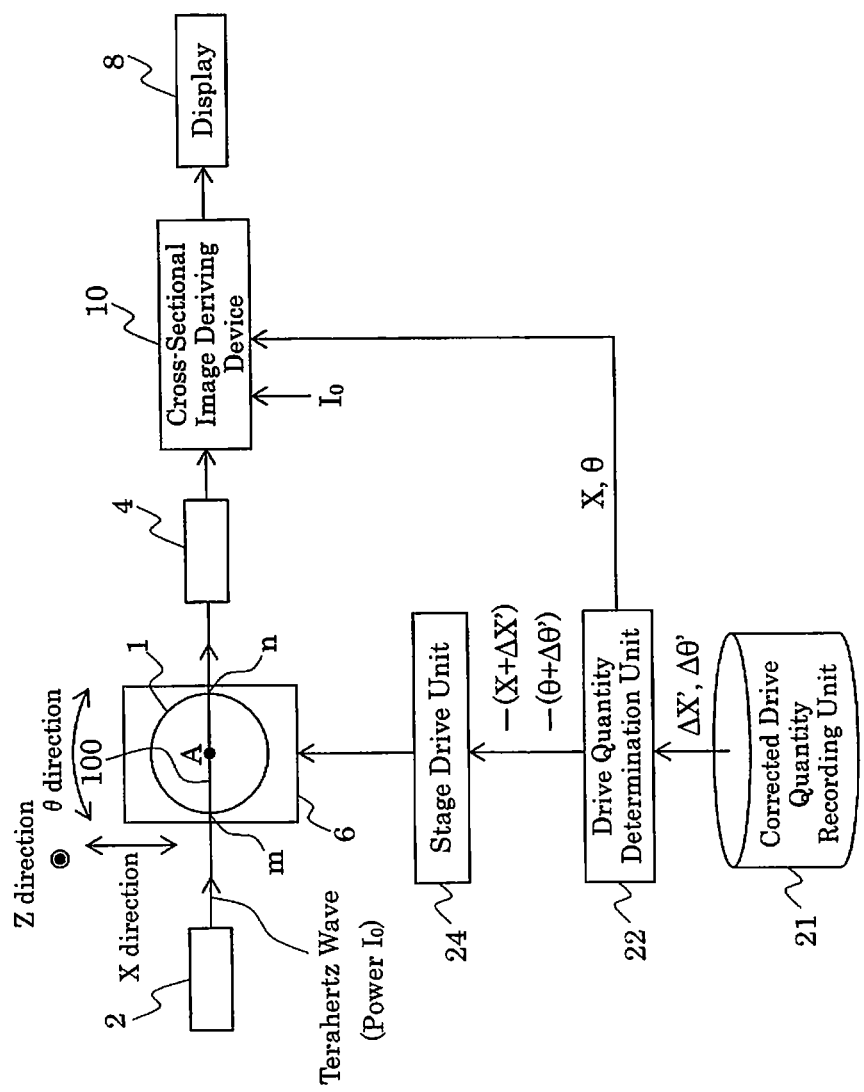
FIG. 11 is a diagram showing a configuration of the electromagnetic wave measurement device according to the second embodiment of the present invention.

FIG. 11 is a diagram showing a configuration of the electromagnetic wave measurement device according to the second embodiment of the present invention. The electromagnetic wave measurement device according to the second embodiment includes the electromagnetic wave output device 2, the electromagnetic wave detector 4, the stage for scanning (relative position changing unit) 6, the display 8, the cross-sectional image deriving device 10, a corrected drive quantity recording unit 21, the drive quantity determination unit 22, and the stage drive unit 24. The electromagnetic wave measurement device is used for measuring the DUT 1. In the following section, the same components are denoted by the same numerals as of the first embodiment, and will be explained in no more details.

The DUT 1, the electromagnetic wave output device 2, the electromagnetic wave detector 4, the stage for scanning (relative position changing unit) 6, and the display 8 are the same as those according to the first embodiment, and hence description thereof is omitted.

The corrected drive quantity recording unit 21 records ΔX' and Δθ'.

Figure 12:
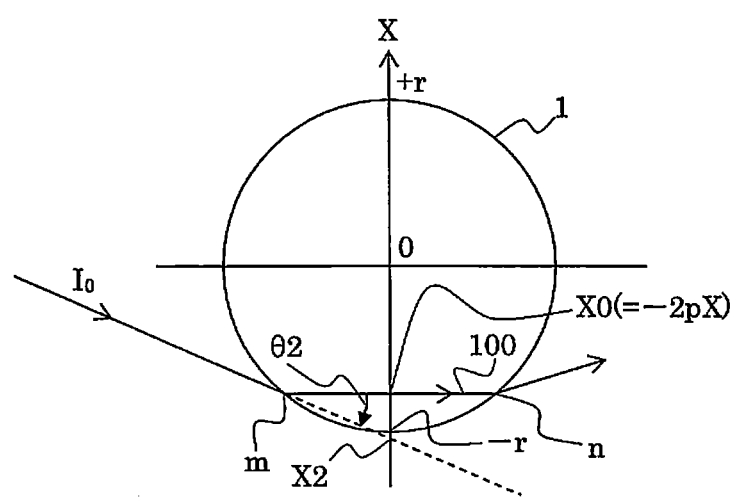
FIG. 12 shows an optical path of the electromagnetic wave when the X intercept of the intersection 100 is X0(=−2pX), and the gradient is 0.

FIG. 12 shows an optical path of the electromagnetic wave when the X intercept of the intersection 100 is X0(=−2pX), and the gradient is 0.

When the refraction of the electromagnetic wave (such as a terahertz wave) by the DUT 1 is considered, the angle of the optical path of the electromagnetic wave traveling toward the DUT 1 with respect to the horizontal axis is θ2 (<0). Moreover, the X coordinate of the point m at which the terahertz wave is made incident to the DUT 1 is −2pX. Then, the X-axis intercept of the optical path of the electromagnetic wave traveling toward the DUT 1 is X2 (<X0).

Moreover, the assumed measured point (−2pX, 0) represents the relative position of the intersection 100 with respect to the DUT 1. In other words, in order to locate the relative position of the intersection 100 with respect to the DUT 1 to the assumed measured point (−2pX, 0), the X-axis intercept of an extension of the optical path of the electromagnetic wave traveling from the electromagnetic wave output device 2 to the DUT 1 (referred to as "traveling optical path") needs to be X2, and the angle of the traveling optical path with respect to the horizontal axis needs to be θ2.

On this occasion, ΔX' is represented as (X-axis intercept of an extension of the actual traveling optical path)−(X coordinate of the assumed measured point), and is recorded in the corrected drive quantity recording unit 21 while ΔX' is associated with the coordinate of the assumed measured point. Δθ' is represented as (angle of the actual traveling optical path with respect to the horizontal axis)−(θ coordinate of the assumed measured point), and is recorded in the corrected drive quantity recording unit 21 while t Δθ' is associated with the coordinate of the assumed measured point.

As for the assumed measured point (−2pX, 0), ΔX'=X2−X0=X2+2pX, and Δθ'=θ2−0=θ2. The ΔX' and Δθ' are recorded in the corrected drive quantity recording unit 21 while they are associated with the assumed measured point (−2pX, 0).

The drive quantity determination unit 22 determines how much the stage for scanning 6 is driven in the X direction and the θ direction. On this occasion, the drive quantity determination unit 22 reads ΔX' and Δθ' corresponding to the assumed measured point (X, θ) from the corrected drive quantity recording unit 21.

On this occasion, a quantity of motion in the X direction of the stage for scanning 6 is −(X+ΔX'), and a quantity of motion in the θ direction is −(θ+Δθ'). The drive quantity determination unit 22 feeds the quantities of motion (−(X+ΔX') and −(θ+Δθ')) of the stage for scanning 6 to the stage drive unit 24. The drive quantity determination unit 22 feeds X and θ to the cross sectional image deriving device 10.

The stage drive unit 24 drives the stage for scanning 6 in the X direction and the θ direction based on the quantities of motion (−(X+ΔX') and −(θ+Δθ')) fed by the drive quantity determination unit 22. As a result, the X-axis intercept of the traveling optical path becomes X+ΔX' and the angle of the traveling optical path with respect to the horizontal axis becomes θ+Δθ'.

Consequently, considering the refraction of the electromagnetic wave (such as terahertz wave) by the DUT 1, the stage for scanning (relative position changing unit) 6 changes the relative position of the intersection 100 with respect to the DUT 1 so that the intersection 100 is at a predetermined relative position (such as the assumed relative position).

For example, considering the refraction of the electromagnetic wave (such as terahertz wave) by the DUT 1, the stage for scanning (relative position changing unit) 6 causes the relative position of the intersection 100 to locate at the assumed measured point (−2pX, 0). In other words, the stage for scanning 6 moves so that the X-axis intercept of the traveling optical path is X+ΔX'=−2pX+X2+2pX=X2, and the angle of the traveling optical path with respect to the horizontal axis is θ+Δθ'=0+θ2=θ2. Thus, the stage for scanning 6 needs to move by −X2 in the X direction, and by −θ2 in the θ direction.

Figure 13:
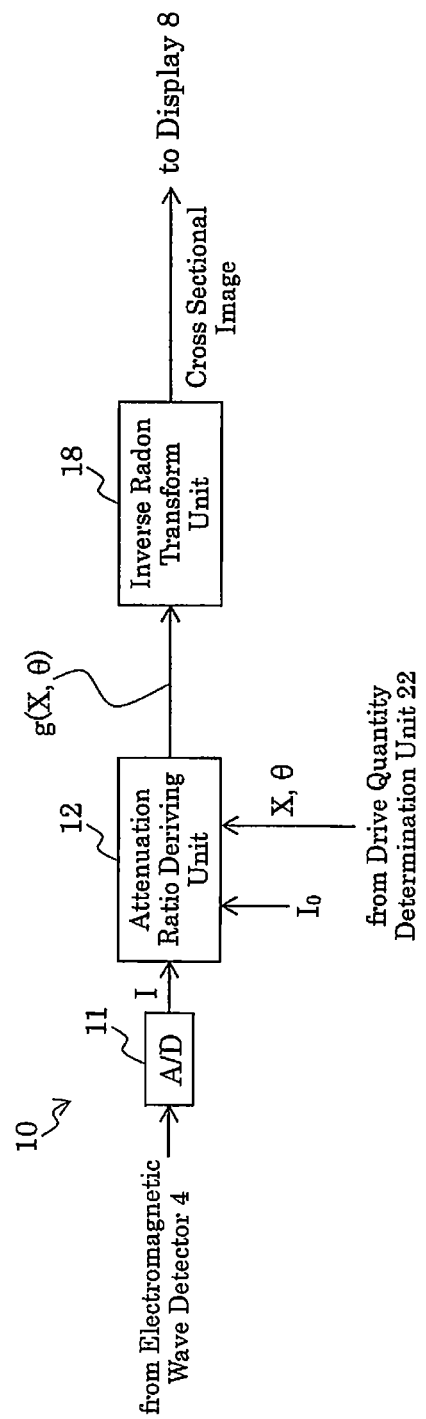
FIG. 13 is a functional block diagram showing a configuration of the cross sectional image deriving device 10 according to the second embodiment.

FIG. 13 is a functional block diagram showing a configuration of the cross sectional image deriving device 10 according to the second embodiment. The cross sectional image deriving device 10 includes the A/D converter 11, the attenuation ratio deriving unit (characteristic value deriving unit) 12, and the inverse radon transform unit 18.

The AD converter 11 is the same as that of the first embodiment, and a description thereof, therefore, is omitted.

The attenuation ratio deriving unit (characteristic value deriving unit) 12 is the same as that of the first embodiment. It should be noted that the attenuation ratio of the electromagnetic wave is associated with (X, θ) acquired from the drive quantity determination unit 22. The point (X, θ) acquired from the drive quantity determination unit 22 is the assumed measured point (predetermined relative position). Thus, the attenuation ratio deriving unit 12 derives the attenuation ratio of the electromagnetic wave while the attenuation ratio is associated with the predetermined relative position (assumed measured point).

The attenuation ratio of the electromagnetic wave is associated with the assumed measured point (refer to FIG. 6), and it is thus appreciated that the sampling widths are even both in X and θ directions. Therefore, it is not necessary to provide the corrected attenuation ratio deriving unit 16, which is different from the first embodiment.

The inverse radon transform unit 18 receives the attenuation ratio g(X, θ) associated with the assumed measured point (refer to FIG. 6) from the attenuation ratio deriving unit 12, and performs the inverse radon transform, thereby acquiring a cross sectional image. The cross sectional image is fed to the display 8. It should be noted that the inverse radon transform unit 18 may determine predetermined colors to be associated with the cross sectional image, and may provide the determined colors to the display 8.

A description will now be given of an operation of the second embodiment.

First, the DUT 1 is fixed to the stage for scanning 6.

The drive quantity determination unit 22 determines how much the stage for scanning 6 is driven in the X direction and the θ direction. On this occasion, the drive quantity determination unit 22 reads ΔX' and Δθ' corresponding to the assumed measured point (X, θ) from the corrected drive quantity recording unit 21. Further, the drive quantity determination unit 22 sets the quantity of motion in the X direction of the stage for scanning 6 to −(X+ΔX'), and the quantity of motion in the θ direction to −(θ+Δθ').

The stage drive unit 24 drives the stage for scanning 6 in the X direction and the θ direction based on the quantities of motion (−(X+αX') and −(θ+Δθ')) fed by the drive quantity determination unit 22. As a result, the X-axis intercept of the traveling optical path becomes X+ΔX' and the angle of the traveling optical path with respect to the horizontal axis becomes θ+Δθ'.

On this occasion, the relative position of the intersection 100 with respect to the DUT 1 is represented as the assumed measured point (X, θ). In other words, the X intercept of the intersection 100 is X (X coordinate of the assumed measured point), and the angle of the intersection 100 with respect to the horizontal axis is θ (θ coordinate of the assumed measured point).

For example, referring to FIG. 12, the stage for scanning 6 is moved by −X2 in the X direction, and by −θ2 in the θ direction so that the X-axis intercept of the traveling optical path is X2, and the angle of the traveling optical path with respect to the horizontal axis is θ2. Then, the relative position of the intersection 100 with respect to the DUT 1 is represented as the assumed measured point (−2pX, 0).

On this occasion, while the stage for scanning 6 is moved in the X direction and the Z direction (direction perpendicular to the sheet of FIG. 1) as well as in the θ direction, the electromagnetic wave output device 2 outputs the electromagnetic wave having a frequency equal to or more than 0.01 [THz] and equal to or less than 100[THz] (such as a terahertz wave) toward the DUT 1. The terahertz wave output to the DUT 1 transmits through the DUT 1. The electromagnetic wave which has passed through the DUT 1 is detected by the electromagnetic wave detector 4. In this way, the DUT 1 is scanned.

The detected result of the electromagnetic wave detector 4 is fed to the A/D converter 11 of the cross sectional image deriving device 10. The detected result of the electromagnetic wave detector 4 is converted by the A/D converter 11 into the digital signal, and the digital signal is fed to the attenuation ratio deriving unit 12.

The attenuation ratio deriving unit 12 derives the attenuation ratio g(X, θ) associated with the assumed measured point (X, θ) where X=−2pX, −pX, 0, pX, and 2pX, and θ=−2pθ, 0, −pθ, pθ, and 2pθ (refer to FIG. 6).

The attenuation ratio g(X, θ) output from the attenuation ratio deriving unit 12 is transformed by the inverse radon transform unit 18 by means of the inverse radon transform, resulting in the cross sectional image. The cross sectional image is colored, and is then displayed by the display 8.

According to the second embodiment, when an electromagnetic wave (frequency thereof is equal to or more than 0.01 [THz] and equal to or less than 100 [THz]) including the terahertz wave is fed to the DUT 1 for measurement, considering that the electromagnetic wave (such as the terahertz wave) is refracted by the DUT 1, the stage for scanning 6 is driven so that the optical path of the electromagnetic wave traveling through the DUT 1 is represented by the assumed measured point. As a result, the adverse effect caused by the refraction by the DUT 1 can be restrained.

Third Embodiment

The configuration of the electromagnetic wave measurement device according to a third embodiment is similar to that of the first embodiment (refer to FIG. 1). However, the configuration of the cross sectional image deriving device 10 according to the third embodiment is different from the configuration of the cross sectional image deriving device 10 according to the first embodiment.

Figure 14:
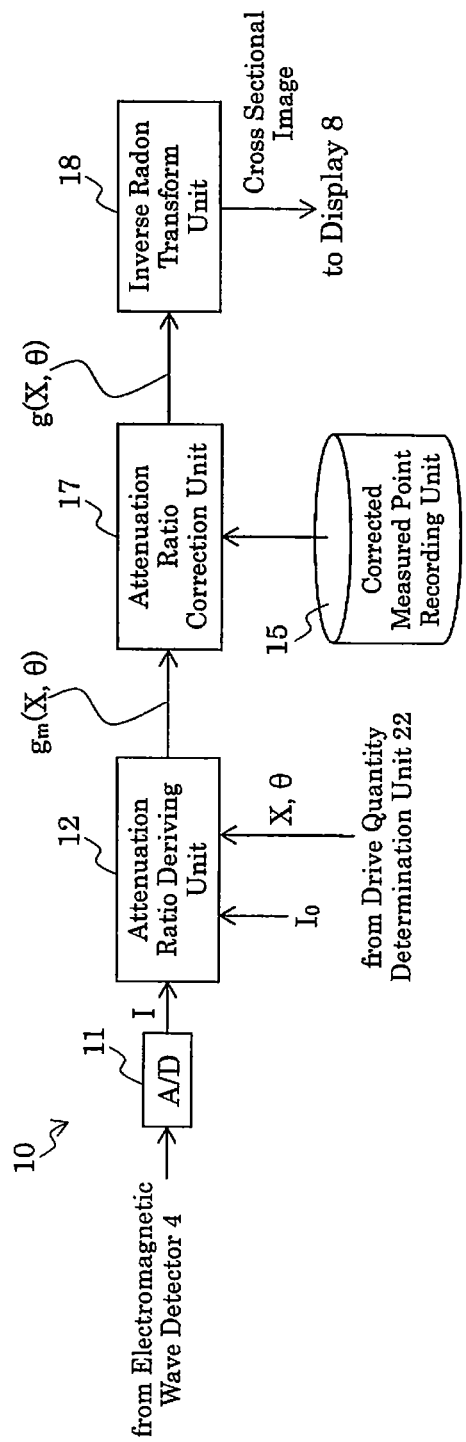
FIG. 14 is a functional block diagram showing the configuration of the cross sectional image deriving device 10 according to the third embodiment of the present invention.

FIG. 14 is a functional block diagram showing the configuration of the cross sectional image deriving device 10 according to the third embodiment of the present invention. The cross sectional image deriving device 10 includes the A/D converter 11, the attenuation ratio deriving unit (characteristic value deriving unit) 12, a corrected measured point recording unit 15, an attenuation ratio correction unit (second association correction unit) 17, and the inverse radon transform unit 18.

The AD converter 11 and the attenuation ratio deriving unit (characteristic value deriving unit) 12 are the same as those of the first embodiment, and a description thereof, therefore, is omitted.

The corrected measured point recording unit 15 associates a predetermined relative position (such as an assumed measured point Q1) and an assumed measured point (such as an assumed measured point Q2) corresponding to an actual measured point closest to the predetermined relative position (such as an actual measured point R2) with each other, and records the associated points.

As described above, the measured point represents a relative position. Moreover, as described above, the measured point representing the assumed relative position is referred to as assumed measured point, and the measured point representing the actual relative position is referred to as actual measured point.

Thus, the corrected measured point recording unit 15 associates the predetermined relative position and the assumed relative position corresponding to the actual relative position closest to the predetermined relative position with each other, and records the associated positions.

Figure 15:
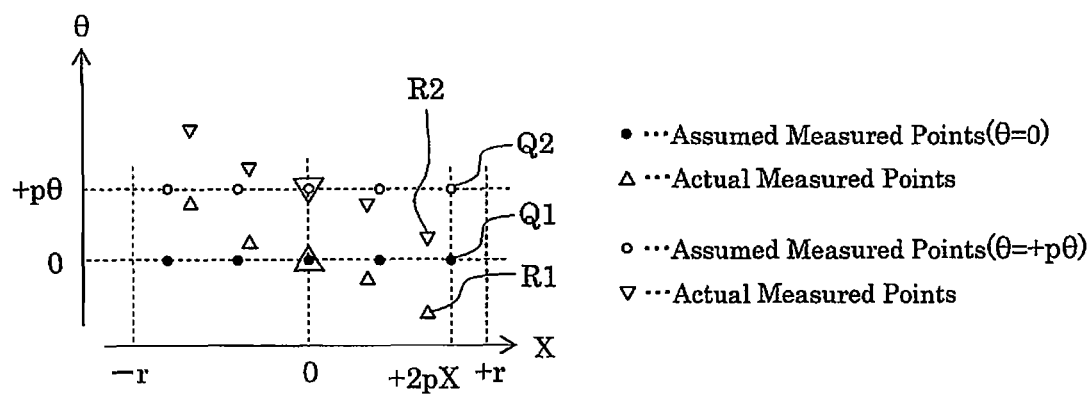
FIG. 15 shows assumed measured points and actual measured points for describing recorded contents of the corrected measured point recording unit 15 according to the third embodiment.

FIG. 15 shows assumed measured points and actual measured points for describing recorded contents of the corrected measured point recording unit 15 according to the third embodiment. It should be noted that actual measured points corresponding to assumed measured points for $\theta=0$ are represented by triangles pointing upward in FIG. 15. Actual measured points corresponding to assumed measured points for $\theta=p\theta$ are represented by triangles pointing downward.

As described in the first embodiment (refer to FIG. 8(*b*)), an actual measured point corresponding to the assumed measured point Q1(2pX, 0) is R1, and is considerably separated from the assumed measured point Q1. On this occasion, an actual measured point corresponding to the assumed measured point Q2(2pX, p$\theta$) is R2, and is closer to the assumed measured point Q1 than the actual measured point R1.

The corrected measured point recording unit 15 associates the assumed measured point Q1 and the assumed measured point Q2 corresponding to the actual measured point R2 closest to the assumed measured point Q1 with each other, and records the associated points. The actual measured point R2 is closer to the assumed measured point Q1 than the actual measured point R1, and, thus, it is appreciated that the attenuation ratio at the assumed measured point Q1 is closer to $g_m(2pX, p\theta)$ (attenuation ratio corresponding to the actual measured point R2) than to $g_m(2pX, 0)$ (attenuation ratio corresponding to the actual measured point R1).

The attenuation ratio correction unit (second association correction unit) 17 receives the attenuation ratio $g_m(X, \theta)$ from the attenuation ratio deriving unit 12. On this occasion, the measured point $(X, \theta)$ represents the assumed relative position (predetermined relative position) of the intersection 100.

On this occasion, the attenuation ratio correction unit 17 reads an assumed measured point corresponding to an actual measured point closest to the assumed measured point $(X, \theta)$ from the corrected measured point recording unit 15. For example, the attenuation ratio correction unit 17 reads the assumed measured point Q2(2pX, p$\theta$) corresponding to the actual measured point R2 closest to the assumed measured point Q1(2pX, 0) from the corrected measured point recording unit 15.

Further, the attenuation ratio correction unit 17 acquires, from the attenuation ratio deriving unit 12, an attenuation ratio associated with the assumed measured point read from the corrected measured point recording unit 15, and associates the acquired attenuation ratio with the assumed measured point $(X, \theta)$ (predetermined relative position). For example, the attenuation ratio correction unit 17 acquires, from the attenuation ratio deriving unit 12, an attenuation ratio $g_m(2pX, p\theta)$ associated with the assumed measured point Q2(2pX, p$\theta$) read from the corrected measured point recording unit 15, and associates the attenuation ratio $g_m(2pX, p\theta)$ with the assumed measured point Q1(2pX, 0) (predetermined relative position). In other words, an association $g(2pX, 0)=g_m(2pX, p\theta)$ is set.

The attenuation ratio correction unit 17 outputs the attenuation ratio $g(X, \theta)$ derived in this way.

The inverse radon transform unit 18 receives the attenuation ratio $g(X, \theta)$ associated with the assumed measured point (refer to FIG. 6) from the attenuation ratio correction unit 17, and performs the inverse radon transform, thereby acquiring a cross sectional image. The cross sectional image is fed to the display 8. It should be noted that the inverse radon transform unit 18 may determine predetermined colors to be associated with the cross sectional image, and may provide the determined colors to the display 8.

A description will now be given of an operation of the third embodiment.

An operation until the attenuation ratio deriving unit 12 derives the attenuation ratio $g_m(X, \theta)$ while the attenuation ratio $g_m(X, \theta)$ is associated with the assumed measured point $(X, \theta)$ (refer to FIGS. 6 and 8) is the same as the operation of the first embodiment.

The attenuation ratio correction unit (second association correction unit) 17 receives the attenuation ratio $g_m(X, \theta)$ from the attenuation ratio deriving unit 12.

Further, the attenuation ratio correction unit 17 reads the assumed measured point corresponding to the measured point $(X, \theta)$ from the corrected measured point recording unit 15. For example, the attenuation ratio correction unit 17 reads the assumed measured point Q2(2pX, pθ) corresponding to the actual measured point R2 closest to the assumed measured point Q1(2pX, 0) from the corrected measured point recording unit 15 (refer to FIG. 15).

Further, the attenuation ratio correction unit 17 acquires the attenuation ratio associated with the assumed measured point read from the corrected measured point recording unit 15 from the attenuation ratio deriving unit 12. The acquired attenuation ratio is associated with the assumed measured point (X, θ) (predetermined relative position). For example, the attenuation ratio correction unit 17 acquires, from the attenuation ratio deriving unit 12, the attenuation ratio $g_m(2pX, pθ)$ associated with the assumed measured point Q2(2pX, pθ) read from the corrected measured point recording unit 15. The attenuation ratio $g_m(2pX, pθ)$ is associated with the assumed measured point Q1(2pX, 0) (predetermined relative position). In other words, an association $g(2pX, 0)=g_m(2pX, pθ)$ is set.

The attenuation ratio correction unit 17 outputs the attenuation ratio g(X, θ) derived in this way.

The inverse radon transform unit 18 receives the attenuation ratio g(X, θ) associated with the assumed measured point (refer to FIG. 6) from the attenuation ratio correction unit 17, and performs the inverse radon transform, thereby acquiring a cross sectional image. The cross sectional image is colored, and is then displayed by the display 8.

According to the third embodiment, when an electromagnetic wave (frequency thereof is equal to or more than 0.01 [THz] and equal to or less than 100 [THz]) including the terahertz wave is fed to the DUT 1 for measurement, it is possible to restrain the adverse effect caused by the refraction of the electromagnetic wave including the terahertz wave by the DUT 1 since the attenuation ratio is derived considering that the electromagnetic wave including the terahertz wave is refracted by the DUT 1.

Moreover, the above-described embodiments may be realized in the following manner. A computer is provided with a CPU, a hard disk, and a media (such as a floppy disk (registered trade mark) and a CD-ROM) reader, and the media reader is caused to read a medium recording a program realizing the above-described respective components such as the cross sectional image deriving device 10, thereby installing the program on the hard disk. This method may also realize the above-described functions.

The invention claimed is:

1. An electromagnetic wave measurement device comprising:
    an electromagnetic wave outputter that outputs an electromagnetic wave having a frequency equal to or more than 0.01 THz and equal to or less than 100 THz toward a device under test;
    an electromagnetic wave detector that detects the electromagnetic wave which has transmitted through the device under test;
    a relative position changer that changes a relative position of an intersection of an optical path of the electromagnetic wave transmitting through the device under test and the device under test, with respect to the device under test;
    a characteristic value deriver that derives a characteristic value of the electromagnetic wave based on a detection result of the electromagnetic wave detector, the characteristic value being associated with an assumed relative position, which is the relative position when it is assumed that the electromagnetic wave is not refracted by the device under test;
    a measured point corrector that changes the assumed relative position to an actual relative position, which is the relative position when the refraction of the electromagnetic wave by the device under test is considered, to associate the result derived by the characteristic value deriver with the actual relative position; and
    a corrected characteristic value deriver that derives the characteristic value associated with a predetermined relative position based on an output from the association corrector.

2. The electromagnetic wave measurement device according to claim 1, wherein the characteristic value is one of an attenuation ratio, a group delay, and a chromatic dispersion of the electromagnetic wave.

3. The electromagnetic wave measurement device according to claim 1, wherein the relative position is represented by an angle between the intersection and a predetermined axis, and a coordinate of an orthogonal axis orthogonal to the predetermined axis at an intersection point between the orthogonal axis and the intersection.

4. An electromagnetic wave measurement device comprising:
    an electromagnetic wave outputter that outputs an electromagnetic wave having a frequency equal to or more than 0.01 THz and equal to or less than 100 THz toward a device under test;
    an electromagnetic wave detector that detects the electromagnetic wave which has transmitted through the device under test;
    a relative position changer that changes a relative position of an intersection of an optical path of the electromagnetic wave transmitting through the device under test and the device under test, with respect to the device under test;
    a characteristic value deriver that derives a characteristic value of the electromagnetic wave based on a detection result of the electromagnetic wave detector, the characteristic value being associated with an assumed relative position, which is the relative position when it is assumed that the electromagnetic wave is not refracted by the device under test; and
    an association corrector that acquires the characteristic value associated with the assumed relative position corresponding to an actual relative position closest to a predetermined relative position, from the characteristic value deriver, and associates the acquired characteristic value with the predetermined relative position, the actual relative position being the relative position when a refraction of the electromagnetic wave by the device under test is considered.

5. The electromagnetic wave measurement device according to claim 4, wherein the characteristic value is one of an attenuation ratio, a group delay, and a chromatic dispersion of the electromagnetic wave.

6. The electromagnetic wave measurement device according to claim 4, wherein the relative position is represented by an angle between the intersection and a predetermined axis, and a coordinate of an orthogonal axis orthogonal to the predetermined axis at an intersection point between the orthogonal axis and the intersection.

7. An electromagnetic wave measurement method using an electromagnetic wave measurement device including: an electromagnetic wave outputter that outputs an electromagnetic wave having a frequency equal to or more than 0.01 THz and equal to or less than 100 THz toward a device under test; an electromagnetic wave detector that detects the electromagnetic wave which has transmitted through the device under test; and a relative position changer that changes a relative position of an intersection of an optical path of the electromagnetic wave transmitting through the device under test and the device under test, with respect to the device under test, the method comprising:

deriving a characteristic value of the electromagnetic wave based on a detection result of the electromagnetic wave detector, the characteristic value being associated with an assumed relative position, which is the relative position when it is assumed that the electromagnetic wave is not refracted by the device under test;

changing the assumed relative position to an actual relative position, which is the relative position when the refraction of the electromagnetic wave by the device under test is considered, to associate the result derived by the deriving of the characteristic value, with the actual relative position; and deriving the characteristic value associated with a predetermined relative position based on a result from the changing of the assumed relative position to the actual relative position.

8. An electromagnetic wave measurement method using an electromagnetic wave measurement device including: an electromagnetic wave outputter that outputs an electromagnetic wave having a frequency equal to or more than 0.01 THz and equal to or less than 100 THz toward a device under test; an electromagnetic wave detector that detects the electromagnetic wave which has transmitted through the device under test; and a relative position changer that changes a relative position of an intersection of an optical path of the electromagnetic wave transmitting through the device under test and the device under test, with respect to the device under test, the method comprising:

deriving a characteristic value of the electromagnetic wave based on a detection result of the electromagnetic wave detector, the characteristic value being associated with an assumed relative position, which is the relative position when it is assumed that the electromagnetic wave is not refracted by the device under test; and acquiring the characteristic value associated with the assumed relative position corresponding to an actual relative position closest to a predetermined relative position, from the result of deriving the characteristic value of the electromagnetic wave, and associating the acquired characteristic value with the predetermined relative position, the actual relative position being the relative position when a refraction of the electromagnetic wave by the device under test is considered.

9. A non-transitory computer-readable medium having a program of instructions for execution by a computer to perform an electromagnetic wave measurement process using an electromagnetic wave measurement device including: an electromagnetic wave outputter that outputs an electromagnetic wave having a frequency equal to or more than 0.01 THz and equal to or less than 100 THz toward a device under test; an electromagnetic wave detector that detects the electromagnetic wave which has transmitted through the device under test; and a relative position changer that changes a relative position of an intersection of an optical path of the electromagnetic wave transmitting through the device under test and the device under test, with respect to the device under test, the computer performing the electromagnetic wave measurement process by:

deriving a characteristic value of the electromagnetic wave based on a detection result of the electromagnetic wave detector, the characteristic value being associated with an assumed relative position, which is the relative position when it is assumed that the electromagnetic wave is not refracted by the device under test;

changing the assumed relative position to an actual relative position, which is the relative position when the refraction of the electromagnetic wave by the device under test is considered, to associate the result derived by the deriving of the characteristic value, with the actual relative position; and deriving the characteristic value associated with a predetermined relative position based on a result from the changing of the assumed relative position to the actual relative position.

10. A non-transitory computer-readable medium having a program of instructions for execution by a computer to perform an electromagnetic wave measurement process using an electromagnetic wave measurement device including: an electromagnetic wave outputter that outputs an electromagnetic wave having a frequency equal to or more than 0.01 THz and equal to or less than 100 THz toward a device under test; an electromagnetic wave detector that detects the electromagnetic wave which has transmitted through the device under test; and a relative position changer that changes a relative position of an intersection of an optical path of the electromagnetic wave transmitting through the device under test and the device under test, with respect to the device under test, the computer performing the electromagnetic wave measurement process by:

deriving a characteristic value of the electromagnetic wave based on a detection result of the electromagnetic wave detector, the characteristic value being associated with an assumed relative position, which is the relative position when it is assumed that the electromagnetic wave is not refracted by the device under test; and acquiring the characteristic value associated with the assumed relative position corresponding to the actual relative position closest to a predetermined relative position from the result of deriving the characteristic value of the electromagnetic wave, and associating the acquired characteristic value with the predetermined relative position, the actual relative position being the relative position when a refraction of the electromagnetic wave by the device under test is considered.

* * * * *